United States Patent [19]

Steppe

[11] Patent Number: 5,474,532
[45] Date of Patent: Dec. 12, 1995

[54] CUTTING BLADE FOR A VITREOUS CUTTER

[75] Inventor: Dennis L. Steppe, Anaheim, Calif.

[73] Assignee: Alcon Laboratories, Inc., Fort Worth, Tex.

[21] Appl. No.: 343,742

[22] Filed: Nov. 22, 1994

[51] Int. Cl.⁶ .................................................. A61B 17/32
[52] U.S. Cl. ...................................................... 604/22
[58] Field of Search .............................. 604/22; 606/159, 606/180, 170, 171, 168, 169, 172–174; 128/751, 752, 753, 754

[56] References Cited

U.S. PATENT DOCUMENTS

| | | |
|---|---|---|
| 1,123,730 | 1/1915 | Greenfield ................................. 606/170 |
| 1,333,745 | 3/1920 | Wescott ....................................... 604/22 |
| 3,512,519 | 5/1970 | Hall .......................................... 606/170 |
| 3,815,604 | 6/1974 | O'Malley et al. . | 
| 4,311,140 | 1/1982 | Bridgman ................................... 604/22 |
| 4,517,977 | 5/1985 | Frost . |
| 4,577,629 | 3/1986 | Martinez . |
| 4,589,414 | 5/1986 | Yoshida et al. . |
| 4,603,694 | 8/1986 | Wheeler . |
| 4,662,869 | 5/1987 | Wright . |
| 4,674,502 | 6/1987 | Imonti . |
| 4,696,298 | 9/1987 | Higgins et al. . |
| 4,735,605 | 4/1988 | Swartz . |
| 4,775,365 | 10/1988 | Swartz . |
| 4,792,327 | 12/1988 | Swartz . |
| 4,850,354 | 7/1989 | McGurk-Burleson et al. . |
| 4,867,155 | 9/1989 | Isaacson . |
| 4,887,613 | 12/1989 | Farr et al. ................................. 606/159 |
| 4,909,249 | 3/1990 | Akkas et al. . |
| 4,986,827 | 1/1991 | Akkas et al. . |
| 5,019,035 | 5/1991 | Missirlian et al. . |
| 5,030,201 | 7/1991 | Palestrant ................................... 604/22 |
| 5,100,426 | 3/1992 | Nixon ......................................... 604/22 |
| 5,112,299 | 5/1992 | Pascaloff ................................... 606/170 |
| 5,176,628 | 1/1993 | Charles et al. . |
| 5,267,955 | 12/1993 | Hanson ..................................... 606/171 |
| 5,269,787 | 12/1993 | Cozean, Jr. et al. ..................... 606/169 |
| 5,284,472 | 2/1994 | Sussman et al. . |

OTHER PUBLICATIONS

Charles, Steve, *Vitreous Microsurgery*, Williams & Wilkins, Baltimore, Md.; 1987; Chapter 2 "Instrument Considerations," pp. 25–41.

*Primary Examiner*—C. Fred Rosenbaum
*Assistant Examiner*—Manuel Mendez
*Attorney, Agent, or Firm*—Jeffrey S. Schira

[57] ABSTRACT

A cutting blade for a rotary vitreous cutter having an opening separated by a cutting bar having two cutting edges so that one of the openings is always in communication with the cutting port in the outer tube of the vitreous cutter as the cutting blade rotates.

7 Claims, 2 Drawing Sheets

CUTTING BLADE FOR A VITREOUS CUTTER

BACKGROUND OF THE INVENTION

This invention relates generally to the field of microsurgical instruments and more particularly to microsurgical instruments used in posterior segment ophthalmic surgery.

The posterior segment (i.e. behind the natural lens) of the eye is filled with a clear, jellylike substance called the vitreous. As a result of disease or trauma to the eye, the vitreous must be removed. A typical microsurgical instrument used in the removal of the vitreous has a hollow outer tube and a hollow inner tube containing a cutting edge. The inner tube generally either reciprocates or rotates within the outer tube. Prior art vitreous cutters are more fully described, for example, in U.S. Pat. Nos. 3,815,604 (O'Malley, et al.), 4,577,629 (Martinez), 4,986,827 (Akkas, et al.), 5,176,628 (Charles, et al.) and 5,284,472 (Sussman, et al.), the entire contents of which are incorporated herein by reference.

Prior art vitreous cutters generally operate by drawing a vacuum in the interior of the inner tube. As the inner tube reciprocates or rotates, this vacuum is introduced to the interior of the eye through a port on the distal tip of the outer tube. When the distal tip is placed near the vitreous, the vacuum causes the vitreous to be drawn through the port and into the interior of the outer needle, where the vitreous is sheared or cut by the cutting blade on the moving inner tube as the edge of the blade slides over the port with a frictional fit. This movement of the inner tube over the port in the outer tube causes the port to be sealed, thereby allowing the vitreous not drawn into the port to spring back to its original position. This movement of the vitreous is not desirable because the vitreous is attached to the retina, and excessive vitreous movement can cause retinal detachment.

One prior art device, disclosed in U.S. Pat. No. 5,284,472 (Sussman, et al.) provides a window or a vent behind the leading edge of the cutting blade so that the vacuum is continuously applied to the vitreous as the vitreous is being cut. The device disclosed in this patent, however, has a reciprocating inner tube that moves longitudinally back and forth along the length the outer tube. In comparison, as can be seen in U.S. Pat. No. 5,176,628 (Charles, et al.), rotary cutters have a cutting blade formed by a notch cut in the inner tube. The Charles, et al., notched rotary cutting blade is substantially similar to the reciprocating vented inner tube of Sussman, et al. With a rotary cutter, as the inner tube rotates, vacuum is applied to the vitreous only so long as the notch in the inner tube is aligned with the port in the outer tube, and as the notched portion of the inner tube rotates out of alignment with the port in the outer tube, the unnotched portion of the inner tube seals the port in the outer tube, thereby releasing the uncut vitreous from the vacuum.

Accordingly, a need continues to exist for a rotary vitreous cutter having a cutting blade that reduces movement of the vitreous during cutting.

BRIEF SUMMARY OF THE INVENTION

The present invention improves upon prior art devices by providing a cutting blade for a rotary vitreous cutter having a plurality of openings separated by a cutting bar with two cutting edges. The use of at least two openings permits one of the openings always to be in communication with the cutting port in the outer tube as the cutting blade oscillates. As a result, vacuum is constantly applied to the vitreous being cut, thereby helping to reduce unwanted vitreous movement.

Accordingly, one objective of the present invention is to provide an improved cutting blade for a rotary vitreous cutter.

Another objective of the present invention is to provide an improved cutting blade for a vitreous cutter that helps to minimize vitreous movement.

Still another objective of the present invention is to provide a vitreous cutter blade with a plurality of openings separated by a cutting bar.

These and other advantages and objectives of the present invention will become apparent from the detailed description, drawings and claims that follow.

DETAILED DESCRIPTION OF THE INVENTION

Cutting blade 10 of the present invention is suitable for use with any rotary vitreous cutter. The preferred rotary vitreous cutter is more completely described in U.S. Pat. No. 5,176,628, which is incorporated herein by reference in its entirety, although any suitable rotary vitreous cutter may also be used. While it is preferred that the rotational movement of the cutting blade be oscillatory, cutting blades having a continuous rotation in a single direction may also be used.

Figure 1:
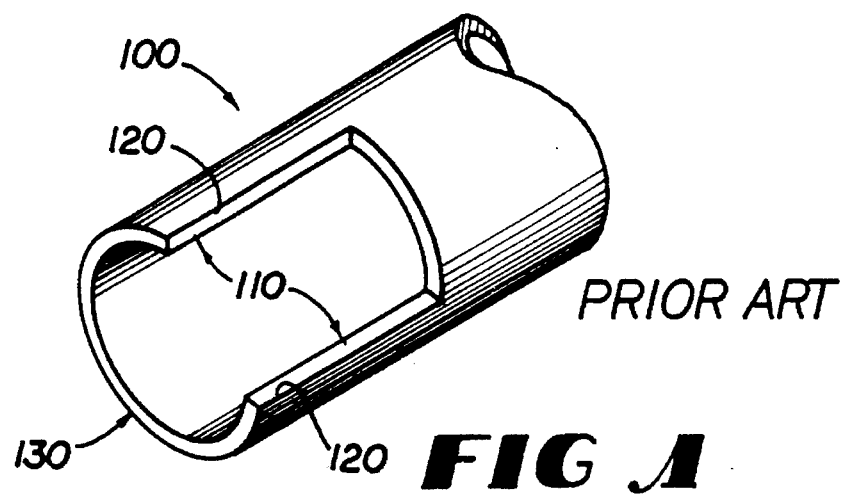
FIG. 1 is an exploded perspective view of a prior art cutting blade suitable for use with a rotary vitreous cutter.

As can be seen in FIG. 1, prior art cutting blade 100 used with rotary vitreous cutters generally contain a notch 110 defining two cutting edges 120. As the blade 110 oscillates, cutting edges 120 shear off any vitreous drawn into notch 110 through the cutting port (item 20 in FIG. 4) in the outer tube (item 22 in FIG. 4); however, as blade 100 oscillates, solid portion 130 of blade 100 seals the cutting port shut for a short period during each cycle, thereby pulsing the vacuum applied to the vitreous.

Figure 2:
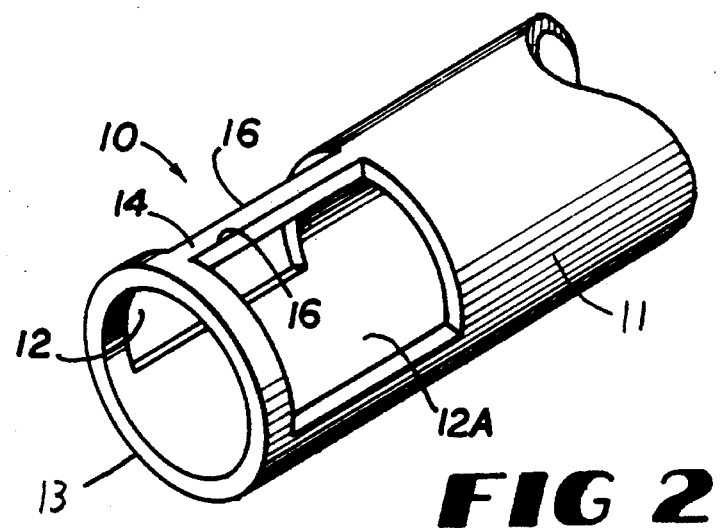
FIG. 2 is an exploded perspective view of the preferred embodiment of the cutting blade of the present invention.
Figure 4:
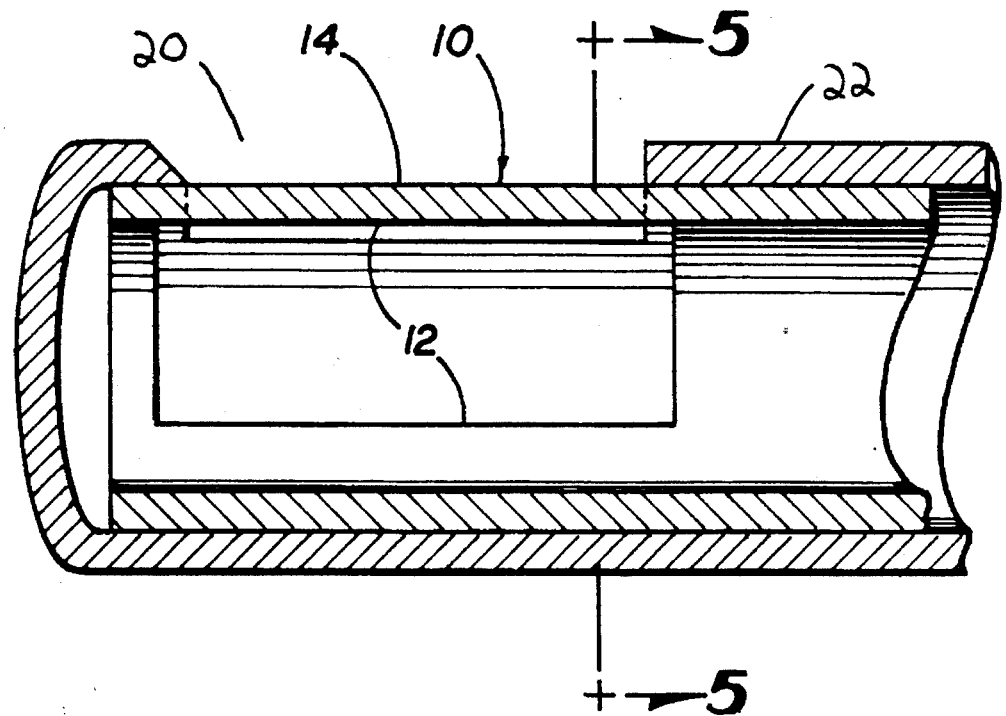
FIG. 4 is a longitudinal cross-section of the cutting blade illustrated in FIG. 2.
Figure 5:
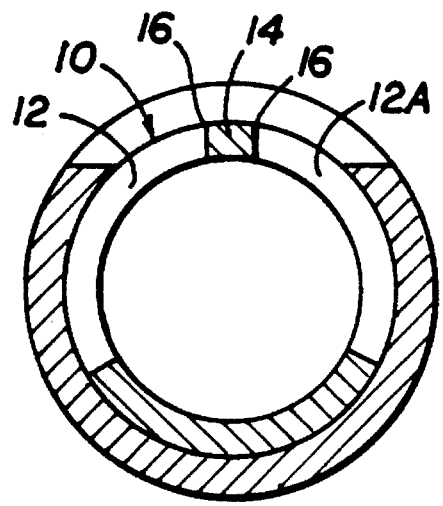
FIG. 5 is a transverse cross section of the cutting blade illustrated in FIG. 2 taken along line 5—5 in FIG. 4.

As can be seen in FIG. 2, cutting blade 10 of the present invention consists of a thin, hollow tube 11 having distal end 13 containing two openings or windows 12 and 12A, defined by cutting bar 14 having two cutting edges 16. Tube 11 is preferably made from medical grade stainless steel or titanium, but other suitable materials may also be used. Tube 11 is preferably approximately 0.25 inches in diameter and preferably 0.005 inches thick. Openings 12 and 12A are preferably 0.020 inches by 0.035 inches and cutting bar 14 is preferably 0.005 inches wide. As best seen in FIGS. 2 and 4, as cutting blade 10 oscillates within outer tube 22, at least one of openings 12 or 12A is constantly in communication with cutting port 20 in outer tube 22, thereby providing for continuous application of vacuum to the vitreous. This continuously applied vacuum reduces the pulsations associated with prior art rotary vitreous cutters.

Figure 3:
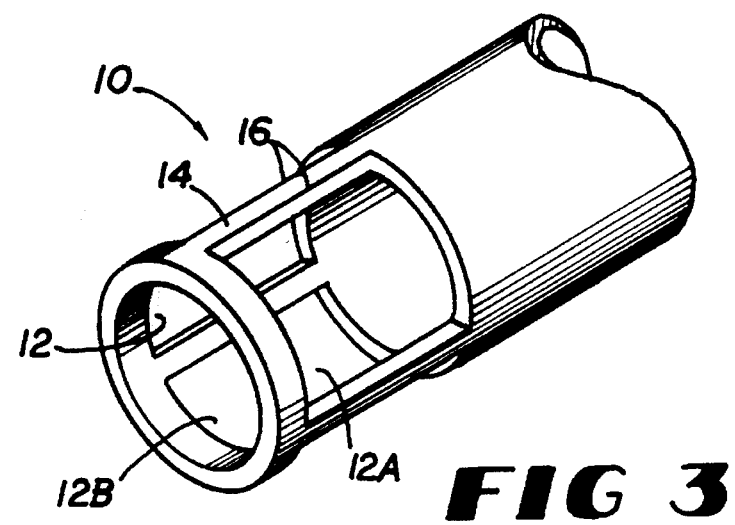
FIG. 3 is an exploded perspective view of a second embodiment of the cutting blade of the present invention.

In a second embodiment of the present invention illustrated in FIG. 3, cutting blade 10' contains a third opening 12B. Openings 12', 12A' and 12B are separated by cutting bars 14' having cutting edges 16'. The embodiment illustrated in FIG. 3 is suitable for use with a continuously rotating vitreous cutter because one of openings 12', 12A' or 12B will always be in communication with the cutting port (item 20 in FIG. 4).

The above examples are meant to be illustrative only. It will be apparent to those skilled in the art that changes or modification may be made to the invention as describe above without departing from its scope or spirit.

I claim:

1. A cutting blade assembly for a rotary vitreous cutter comprising,
   a. an outer tube;
   b. a thin, hollow inner tube having a distal end received within the outer tube; and
   c. at least two openings on the distal end separated by a cutting bar, the cutting bar being smaller than the openings.

2. The cutting blade assembly of claim 1 wherein the tubes comprise stainless steel.

3. The cutting blade assembly of claim 1 wherein the tubes comprise titanium.

4. The cutting blade assembly of claim 1 wherein the distal end contains three openings.

5. A cutting blade assembly for a rotary vitreous cutter comprising,
   a. an outer tube;
   b. a thin, hollow, metal inner tube having a distal end received within the outer tube; and
   c. three openings on the distal end separated by a plurality of cutting bars, the cutting bars being smaller than the openings.

6. The cutting blade assembly of claim 5 wherein the tubes comprise stainless steel.

7. The cutting blade assembly of claim 5 wherein the tubes comprise titanium.

* * * * *